United States Patent [19]

Martin et al.

[11] Patent Number: 5,296,370
[45] Date of Patent: Mar. 22, 1994

[54] REPAIR MEDIUM FOR THE RESUSCITATION OF INJURED CELLS

[75] Inventors: Alain Martin, Ringoes; Stanley E. Katz, Milltown, both of N.J.

[73] Assignee: Rutgers, The State University, Piscataway, N.J.

[21] Appl. No.: 961,207

[22] Filed: Oct. 14, 1992

Related U.S. Application Data

[63] Continuation of Ser. No. 592,513, Oct. 4, 1990, abandoned.

[51] Int. Cl.$^5$ ............... C12N 1/00; C12N 1/12; C12N 1/20; C12N 1/04; C12N 5/00
[52] U.S. Cl. ............... 435/252.1; 435/240.1; 435/240.3; 435/243; 435/253.6; 435/260
[58] Field of Search ............ 435/240.1, 240.3, 240.31, 435/240.54, 243, 252.1, 253.6, 260

[56] References Cited

PUBLICATIONS

Pp. 281-291 of the 1989 edition of *Bergy'Manual*.
Pp. 1237-1238 of Bailey and Scott, *Microbiology*.
*Lipid Pharmacology* (Paoletti, Ed., Academic Press, New York, 1964).
Martin et al., *J. Assoc. Off. Anal. Chem.*, 74(3), pp. 522-525, 1991.
Martin, *a Resuscitation Medium for the Rapid Recovery and Isolation of Injured Salmonella, Escherichia coli, Staphylococcus ureus, and Listeria in Food* (Rutger University, Oct. 30, 1989).
Mossell, *J. Assoc. Off. Anal. Chem.*, 74(1), 1-13 (1991).
*Composition of Oils and Fats*, Theobald Industries, (publication date unknown).
D'Aoust, *Appl. Environ. Microbiol.*, 35(3), pp. 483-486 (1978).
Murthy, *J. Food Microbiol.*, 4(4), pp. 341-346 (1986).
Brewer et al., *Appl. Environ. Microbiol.*, 34(6), 797-800 (1977).
Rayman et al., *Can. J. Microbiol.*, 24(7), 883-85 (1978).
McDonald et al., *Appl. Environ. Microbiol.* 45(2), 360-5 (1983).
Alico et al., *Appl. Environ. Microbiol.*, 51(4), 699-702 (1986).
Mackey et al., *J. Appl. Bacteriol.*, 53(2), 233-42 (1982).
Park et al., *Can. J. Microbiol.*, 23(5), 559-62 (1977).
Russell et al., *Appl. Microbiol.*, 16(2), 335-9 (1968).
Allyn, *J. Bacteriol.*, 20, 417-39 (1930).

*Primary Examiner*—Douglas W. Robinson
*Assistant Examiner*—Susan M. Dadio
*Attorney, Agent, or Firm*—Lerner, David, Littenberg, Krumholz & Mentlik

[57] ABSTRACT

A cell treatment composition based on a non-selective complete nutrient medium and also including a yeast derivative, one or more antioxidants, an oxygen tension reducing agent and one or more fatty acids between 10 and 25 carbon atoms in length having from 0 up to 4 double bonds. Nutrient medium additives for treatment of injured, damaged or stressed cells containing a yeast derivative, one or more antioxidants, an oxygen tension reducing agent and one or more fatty acids between 10 and 25 carbon atoms in length having from 0 up to 4 double bonds. Methods for treating prokaryotic and eukaryotic cells, including the steps of providing one or more injured, damaged or stressed cells and supplying the cells with an environment that includes a non-selective complete nutrient medium and also contains a yeast derivative, one or more intracellular antioxidants, oxygen tension reducing agent and one or more fatty acids between 10 and 25 carbon atoms in length having from 0 to 4 double bonds.

22 Claims, No Drawings

REPAIR MEDIUM FOR THE RESUSCITATION OF INJURED CELLS

This is a continuation of application Ser. No. 07/592,513, filed Oct. 4, 1990, now abandoned.

BACKGROUND OF THE INVENTION

The present invention relates to compositions for the treatment of injured, damaged or stressed cells, and in particular to a composition for promoting the repair of both prokaryotic and eukaryotic cells. The present invention also relates to methods for treating cells with the compositions of the present invention.

Environmental stresses due to heat, freezing, low pH, irradiation, trauma and the like can damage cellular membrane integrity, resulting in cell populations that require more exacting growth requirements for repair and proliferation. One characteristic of injured cells is their inability to tolerate growth conditions in which normal cells would multiply. Providing injured cells with an environment that promotes the repair of cellular membrane damage restores the injured cells to a sound physiological condition that enables the cells to tolerate the growth conditions in which normal cells flourish.

In the case of food pathogens, microorganisms damaged by food processing techniques can escape detection in food samples contaminated therewith. Providing microorganisms with an environment that restores the injured cells to sound physiological condition prevents the injured cells from escaping detection.

One impediment to the proliferation of damaged or stressed cells recognized by the prior art is the susceptibility of such cells to the accumulation of relatively low levels of hydrogen peroxide in the cell cytoplasm. Brewer, *Appl. Environ. Biol.*, 34(6), 797–800 (1977), Rayman, *Can. J. Microbiol.*, 24(7), 883–5 (1978) and McDonald, *Appl. Environ. Microbiol.*, 45(2). 360–5 (1983) disclose the beneficial effects to injured cells of supplementing growth media with compounds that degrade hydrogen peroxide or block its formation, including sodium pyruvate.

The importance of antioxidants such as pyruvate in media for treating injured cells is also disclosed by D'Aoust, *Appl. Environ. Microbiol.*, 35(3), 483–6 (1978), Alico, *Appl. Environ. Microbiol.*, 51(4), 699–702 (1986) and Mackey, *J. Appl. Bacteriol.*, 53(2), 233–42 (1982).

Park, *Can. J. Microbiol.*, 23(5), 559–62 (1977) and D'Aoust, *Appl. Environ. Microbiol.*, 35(3), 483–6 (1978) disclose growth media beneficial to injured cells. Supplementation of growth media with yeast extract was disclosed to nurture injured cells by Russell, *Appl. Microbiol.*, 16(2), 335–9 (1986). Murthy, *J. Food Microbiol.*, 4(4), 341–6 (1986) discloses supplementation of growth media with unsaturated fat to resuscitate injured cells. The importance of anaerobic conditions to the resuscitation of injured aerobic bacteria is disclosed by Allen, *J. Bacteriol.*, 20, 417–39 (1930).

SUMMARY OF THE INVENTION

A treatment composition has now been discovered that exhibits superior performance in promoting the growth of injured, damaged or stressed cells over the prior art compositions containing nutrient media supplemented with sodium pyruvate, unsaturated fats or yeast extract alone. It has now been discovered that an environment in which injured, damaged or stressed cells flourish can be obtained by treating the cells with a composition based upon a non-selective complete nutrient medium supplemented with one or more antioxidants, a yeast derivative, an agent capable of reducing oxygen tension in the medium, and one or more fatty acids between 10 and 25 carbon atoms in length having from 0 up to 4 double bonds.

Although it is known to supplement nutrient media with yeast derivatives or an antioxidant such as pyruvate, or with unsaturated fatty acids, to nurture injured cells, the growth rate of injured, damaged or stressed cells in the treatment composition of the present invention is synergistically greater than the growth rates of such cells in media supplemented with yeast derivatives, antioxidant, an oxygen tension reducing agent, or fatty acids alone. Stated another way, the treatment composition of the present invention stimulates the repair of cells and the growth rate for injured, damaged or stressed cells greater than the combined individual growth or repair rates of such cells in complete nutrient media, yeast derivatives, antioxidants, oxygen tension reducing agent, pyruvate or fatty acid supplemented media alone.

Therefore, according to one aspect of the present invention, there are provided complete nutrient medium additives for the treatment of injured, damaged or stressed cells containing yeast derivatives, one or more antioxidants, an agent capable of reducing oxygen tension in the medium, and one or more fatty acids between 10 and 25 carbon atoms in length having from 0 up to 4 double bonds. The additive is added to a non-selective nutrient medium containing all the nutrient components necessary to the cells to be grown to provide a composition for the treatment of injured, damaged or stressed cells.

The additive of the present invention may also be prepared in combination with a complete nutrient medium. Accordingly, another aspect of the present invention provides a cell treatment composition based upon non-selective complete nutrient media supplemented with yeast derivatives, one or more antioxidants, an agent capable of reducing oxygen tension in the medium, and one or more fatty acids between 10 and 25 carbon atoms in length having from 0 up to 4 double bonds.

The present invention also includes methods for treating injured, damaged or stressed cells using the treatment composition of the present invention. Therefore, according to another embodiment of the present invention, a method is provided for treating injured, damaged or stressed cells, including the steps of providing one or more injured, damaged or stressed cells and supplying the cells with an environment that includes a non-selective complete nutrient medium supplemented with a yeast derivative, one or more antioxidants, an agent capable of reducing oxygen tension in the medium, and one or more fatty acids between 10 and 25 carbon atoms in length having from 0 up to 4 double bonds.

The present invention incorporates the discovery that the growth of injured, damaged or stressed cells is promoted by providing the cells with an environment that includes a complete source of nutrients that also contains certain additives. The one or more antioxidants are added to degrade or prevent the formation of hydrogen peroxide, and related oxygen radicals in the cell cytoplasm, as well as exterior to the cell. The yeast derivatives are added as sources of heat shock proteins, growth factors and other agents the action of which in promoting cell growth and repair is not completely understood. The agent capable of reducing oxygen tension in the medium is added to maintain the environment in an anaerobic state. The fatty acids are those required by cells, including fatty acids necessary for membrane repair, that the cells are not capable of generating under anaerobic conditions.

The media additives and treatment compositions of the present invention are all-purpose in scope and suitable for the treatment of populations of a variety of injured, damaged or stressed prokaryotic and eukaryotic cells, including eukaryotic cell tissues. Other features and advantages of the compositions and methods of the present invention will be more readily apparent from the detailed description of the preferred embodiment set forth below.

DETAILED DESCRIPTION OF THE PREFERRED EMBODIMENT:

The treatment compositions of the present invention are based on non-selective complete media for supporting cell growth. Any complete media containing the nutrients required by injured, damaged or stressed cells to recover is suitable for use in the present invention. A "complete" medium is defined as one capable of supplying all nutrients required by the cells to be grown, which will vary with cell type but will be clear to one of ordinary skill in the art. The medium may be simple or complex, so long as it is complete. Exemplary nutrients in complete medium include carbohydrates, amino acids, peptides, proteins, nucleic acids, nucleotides, fats, fatty acids, triglycerides, minerals and vitamins. Non-selective complete media are used so that the composition will support the growth of a variety of microorganisms and other cell types.

Non-limiting examples of typical media suitable for use with the present invention includes tryptic soy broth, nutrient broth, Eagle's media, yeast mold broth and the like. The media disclosed by Perk, *Can. J. Microbiol.*, 23(5), 559-62 (1977) and D'Aoust, Appl. Environ. Microbiol., 35(3), 43-6 (1978) are also suitable for use with the present invention. The disclosures of these two references are incorporated herein by reference thereto. The most preferred medium is tryptic soy broth, which is substantially equivalent to trypticase soy broth.

The concentration of the nutrient media may be between about one-half and about four times the normal concentration recommended by the media manufacturer, typically between about 2.5 and about 20 weight percent. One to two times the normal concentration is preferred, or between about five and about ten weight percent. The nutrient media base is prepared in the conventional manner according to manufacturer's directions, usually by dissolving the desired quantity of media in an appropriate quantity of sterile distilled water at room temperature followed by autoclaving at elevated temperature and pressure.

Injured, damaged or stressed cells tend to accumulate hydrogen peroxide in the cell cytoplasm, as well as related oxygen radicals. Accordingly, the cell treatment compositions of the present invention also include one or more antioxidants, which function to degrade hydrogen peroxide and related oxygen radicals or block their formation in the cell cytoplasm, as well as in the environment surrounding the cells. Exemplary intracellular antioxidants suitable for use with the present invention are described in McDonald, *Appl. Environ. Microbiol.*, 45(2), 360-5 (1983) and D'Aoust, *Appl. Environ. Microbiol.*, 35(3), 43-6 (1978), the disclosures of both of which are incorporated herein by reference thereto. Among the preferred antioxidants are pyruvate, succinate, glutathione, catalase, selenium, albumen, glucose, butylated hydroxy anisole (BHA), butylated hydroxy toluene (BHT), ascorbic acid, lactic acid, uric acid, superoxide dismutase, glutathione peroxidase and n-acetyl cysteine. Pyruvate is the most preferred antioxidant because it functions effectively both in the cytoplasm a well as the cell environment, and it is a metabolite of the Kreb's cycle and generally functions to reverse cytotoxicity and increase cellular proliferation beyond that function contributed by its antioxidant nature. In preferred compositions according to the present invention, one of the one or more antioxidants is sodium pyruvate.

In another preferred embodiment of the present invention, the one or more antioxidants includes one or more membrane bound antioxidant, which function to stabilize damaged cell membranes and to promote membrane repair. Examples of membrane bound antioxidants include vitamin E and beta-carotene.

Any minimal amount of antioxidant will function to promote the repair of injured, damaged or stressed cells, although the amount present should not exceed 5% by weight. Acceptable results are achieved with between about 0.10 and 1.0% levels, and best results are achieved with levels between about 0.25 and about 0.75%.

The present invention incorporates the discovery that the addition of yeast derivatives to a cell growth medium promotes the growth or repair of injured, damaged or stressed cells. It is believed that the growth factors and heat shock proteins contained in yeast derivatives significantly contribute to the promotion of cell growth and repair. It is also believed that other factors are present in yeast derivatives, presently unidentified, that additionally contribute to the promotion of cell growth and repair.

Examples of yeast derivatives suitable for use with the present invention include yeast extract, live yeast cell derivative, autolyzed yeast and the like, and mixtures thereof. Yeast extract is particularly preferred because it is economical in cost.

The use of yeast derivatives is particularly advantageous because in addition to being a source of growth factors and heat shock proteins, yeast derivatives also supply B-complex vitamins, carbohydrates, amino acids, proteins, nucleic acids, nucleotides, minerals, triglycerides, fatty acids important for membrane repair, particularly oleic and palmitic acids, and glutathione.

Any minimal amount of yeast derivative will promote the repair of injured, damaged or stressed cells, although the amount present should not exceed about 5.0% by weight. Acceptable results are obtained with between about 0.10 and about 1.0% and best results were obtained with about 0.50% yeast derivative.

The present invention further incorporates the discovery that repair of injured, damaged or stressed cells is promoted in an anaerobic environment, which also tends to block the formation of hydrogen peroxide and related oxygen radicals. The compositions of the present invention therefore also include an agent for reducing the oxygen tension of the complete nutrient media base to provide such an anaerobic environment. The oxygen tension reducing agents also function to scavenge oxygen radicals in the environment surrounding the cell, which also promotes cell growth. Preferred oxygen tension reducing agents include sodium thioglycollate, and cysteine. Sodium thioglycollate is a preferred oxygen tension reducing agent because it also binds toxic heavy metals that may be present in the environment to further promote cell proliferation.

Any minimal amount of oxygen tension reducing agent present will promote the repair of injured, damaged or stressed cells, although the amount present should not exceed 5.00% by weight. Improved results are achieved with levels between about 0.0025 and about 0.5%, and best results are achieved with a level between about 0.005 and about 0.10%.

Cellular production of saturated and unsaturated fatty acids needed for membrane repair occurs slowly under the anaerobic conditions created by the presence of the oxygen tension reducing agents in the compositions of the present invention. For this reason, one or more fatty acids from 10 to 25 carbon atoms in length having from 0 up to 4 double bonds are added to the composition of the present invention to supplement the cell's ability to make such fatty acids. Preferably, at least one of the fatty acids added to the composition of the present invention should be unsaturated. The saturated and unsaturated fatty acids selected for inclusion in the compositions of the present invention will depend upon the membrane requirements of the cells to be treated. For example, *E. coli* only requires oleic acid for membrane repair.

The one or more fatty acids of the compositions of the present invention are preferably between 12 and 20 carbon atoms in length and have from 0 up to 3 double bonds. The preferred range of fatty acids can be obtained by adding to the compositions of the present invention one or more animal or vegetable fats. Chicken fat is especially preferred, because this fat alone contains a complete mixture of the preferred range of saturated and unsaturated fatty acids.

Any minimal amount of the fatty acids will promote the repair of injured, damaged or stressed cells, although the amount present should not exceed 5.0% by weight. Improved results are obtained with fatty acid levels between about 0.025 and about 1.0 percent by weight, and best results are obtained with levels between about 0.05 and about 0.5% by weight.

The compositions of the present invention may also optionally further include an emulsifier to compatibilize the one or more animal or vegetable fats with the media base. Examples of emulsifiers include Tween 80.

In addition to fatty acids, proteins are also required for membrane repair. The nutrient media on which the compositions of the present invention are based function as a source of such proteins. However, depending upon the media chosen, and the concentration used, the media may not be a sufficient source of such protein. The compositions of the present invention preferably contain at least 0.1% protein and therefore may optionally include a protein supplement to provide this protein level. Examples of suitable protein supplements include casammino acids, brain-heart infusion and proteous peptone. Any minimal amount of protein supplement will promote the repair of injured, damaged or stressed cells, although the amount present should not exceed about 5.0% by weight. Acceptable results are obtained with between about 0.10 and about .0% and best results were obtained with about 0.50% protein supplement.

A preferred treatment composition in accordance with the present invention will contain 0.25% by weight sodium pyruvate, 0.01% by weight sodium thioglycollate, 0.10% by weight chicken fat and 0.50% by weight yeast extract in a normal concentration (3.0% by weight of dried medium in sterile distilled water) of tryptic so broth.

The present invention also includes nutrient medium additives combining the yeast derivatives, antioxidants, oxygen tension reducing agent, fatty acids and optional protein supplements of the present invention for addition to a non-selective complete nutrient medium to provide a composition for the treatment of injured, damaged or stressed cells.

Typically, the additives of the present invention contain between about 5.0 and about 15% by weight yeast derivative, between about 5.0 and about 15% by weight antioxidant, between about 0.125 and about 7.5% by weight oxygen tension reducing agent, and between about 1.25 and about 15% by weight fatty acids. The additives may also optionally include between about 1.0 and about 10% by weight of a protein supplement.

The additives of the present invention may be added to the non-selective complete nutrient media of the present invention at levels between about 1.0 and about 30.0% by weight. The combination provides compositions for the treatment of injured, damaged or stressed cells that satisfy the requirements for the treatment compositions of the present invention.

The compositions of the invention may be formulated using techniques known in the art. An exemplary procedure involves adding the ingredients separately, or in various combinations, to sterile distilled water with mixing at room temperature for a period of time sufficient to dissolve the ingredients. The compositions are then autoclaved at 121° C., 15 pounds pressure for 15 minutes.

Alternatively, all or some of the ingredients may be filter sterilized to prevent degradation of heat sensitive components. For example, the yeast derivatives contain glycoproteins sensitive to sugar caramelization that occurs during autoclaving. Filter sterilization by way of a 0.22 micron filter is preferred.

Similarly, the nutrient medium additives of the present invention are added prior to sterilizing to nutrient media with mixing at room temperature for a period of time sufficient to dissolve the additives, followed by autoclaving at 121° C., 15 pounds pressure for 15 minutes. Again, some or all of these materials may be filter sterilized.

Techniques associated with the preparation of the compositions of the invention are well known, and the present method may vary somewhat depending upon the specific product to be manufactured without departing from the essential parameters relating to the preparation of nutrient media for cell growth. The exemplary procedure is presented for purposes of illustration and to provide a best mode for the practice of the invention, and therefore, the invention should not be limited to these parameters.

The cell treatment compositions of the present invention and the methods for preparing the compositions of the invention may be used for treating injured, damaged or stressed cells. A method of treatment in accordance with the present invention involves providing one or more injured, damaged or stressed cells and supplying the cells with an environment containing a non-selective complete nutrient medium, yeast derivatives, one or more antioxidants, an oxygen tension reducing agent, and one or more fatty acids 10 to 25 carbon atoms in length from 0 up to 4 double bonds.

The compositions of the present invention are useful in the resuscitation of microbial populations injured, damaged or stressed by food processing, fermentation or other conditions. Injured cells constitute a high proportion of the microbial population in processed foods and escape detection by conventional methods that do not incorporate a resuscitation step needed for the recovery of injured cells. The compositions of the present invention can rapidly enhance the recovery of injured pathogens in a sample prior to making the sample selective for the isolation of a desired pathogen.

Among the microbial populations resuscitated by the compositions of the present invention are important food borne pathogens including members of the genera Staphylococcus and Listeria and the family Enterobacteraciae, which includes the genus Salmonella and E. coli.

Because the compositions of the present invention enhance the recovery of a variety of potential food contaminant organisms, when a food sample is suspected of being contaminated with one or more of the types of microorganisms listed above, a single resuscitation step need only be performed prior to dividing the sample into sub-samples for individual selective testing for a particular microorganism. In the past, a specific resuscitation medium was required for each expected microorganism. The treatment composition of the present invention reduces the time and cost needed to detect pathogens in food.

When the treatment method of the present invention is used as a resuscitation step for the isolation of food pathogens, the treatment method will further include steps that provide cells with a growth media selective for a predetermined cell species after the cells have substantially recovered from injury, damage or stress. This method will preferably include the step of reproducing the cells in the treatment environment so that the cells recover from injury, damage or stress prior to transferring the cells to a selective growth medium, or adding ingredients making the medium selective. Preferably, these cells are grown in the treatment environment for between about 2 and about 24 hours, depending upon the sample size and cell population density, more preferably between about 3 and about 5 hours, and most preferably for about 4 hours.

While the treatment compositions are particularly suitable as media for the growth or storage of injured or damaged cells, the compositions of the present invention also promote the growth of prokaryotic and eukaryotic cells in fermentation processes, increasing the tolerance of such cells for fermentation product toxins that otherwise stress the cells. Accordingly, use of the treatment compositions of the present invention as a growth media increases the production efficiency by prokaryotic and eukaryotic cells of alcohol, antibiotics, recombinant genetic products and the like. The treatment compositions can also be used in the field of recombinant genetics as growth media to increase yields in the development of recombinant cell lines.

As indicated above, the treatment compositions of the present invention also promote the repair of injured or damaged eukaryotic cell tissues. The compositions of the present invention can be formulated with conventional adjuvants to form pharmaceutical compositions, medicaments and the like for the treatment of injured, damaged or stressed tissues. The compositions of the invention can also be used in combination with conventional medicaments for the treatment of cell or tissue injury.

The foregoing end use applications are listed to illustrate fields of use for the treatment compositions and methods of the present invention and are not intended to be limiting of same. The following example is given to illustrate the invention, but is not deemed to be limiting thereof. All percentages given throughout the specification are based upon weight, unless otherwise indicated.

EXAMPLE

A cell treatment composition is prepared by adding to one liter of sterile distilled water 30 g dehydrated tryptic soy broth medium from Difco of Detroit, Mich., 2.5 g sodium pyruvate from Sigma Chemical of St. Louis, Mo., 0.10 g sodium thioglycollate from Sigma Chemical, 1.0 g chicken fat from Capitol City Products Company of St. Louis, Mo., and 5.0 g yeast extract from Difco. The mixture is stirred at room temperature until the ingredients are dissolved or suspended in the water, about 10 minutes. The solution is then sterilized by autoclaving at 121° C. at 15 pounds pressure for 15 minutes.

Foods naturally contaminated with Salmonella are used for comparison of the FDA's Bacteriological Analytical Manual (BAM) methods for the resuscitation and isolation of Salmonella to an isolation method using the cell treatment composition of the example as a resuscitation medium. The foods are obtained from industrial sources and known to have a high probability of being contaminated with low levels of Salmonella. The foods examined are egg products, frozen chicken parts, peppers, spices and onions. 50-gram samples of the contaminated foods are placed in 250 mLs of sterile water and mixed using blenders. The blended sample mixtures are divided equally into two 125 mL fractions. For the FDA/BAM method, 125 mLs of a double strength solution of sterile lactose broth is placed into one set of samples, mixed and incubated for 24 hours at 35° C., as prescribed by the BAM method. The other sample is diluted with a double strength concentration of the composition of the example, mixed and incubated for four hours at 35° C. At the end of the four hours, the sample that was placed into the example composition is divided equally, and the selective agents found in tetrathionate medium are added to one sample and the selective agents found in selinite cystoine medium are added to the other sample. The samples are then incubated overnight.

The next morning, the presence of Salmonella in the samples is then checked within four hours using a Salmonella-specific monoclonal antibody ELISA test kit manufactured by Oganono Teknika of Durham, N.C. The test is performed in accordance with the manufacturer's instructions and the results are depicted in Table I. The results are confirmed using conventional plating techniques.

With the BAM control samples, 1 mL samples from the lactose broth are transferred into tetrathionate and selinite cysteine broth and incubated for another 24 hours. The next day, the presence of Salmonella is checked using the ELISA test kit. The results are also confirmed, using BAM-prescribed techniques. The results are also shown in Table I.

Referring to Table I, the results demonstrate the superiority of the treatment composition of the present invention when used as a resuscitation medium over the conventional BAM method. The BAM method confirmed the presence of Salmonella in three samples of the egg product, while the experimental method using the treatment composition of the present invention as a resuscitation medium confirmed the presence of Salmonella in 9 samples. The Salmonella in the egg products were stressed or injured by a hydrogen peroxide pasteurization process. Without the four hour resuscitation period in the treatment composition medium of the example, the stressed Salmonella were not detected by the conventional method. The inability to detect the Salmonella can pose a potentially serious health risk to people who consume processed eggs.

TABLE I

| FOOD TESTED | SAMPLES TESTED | POSITIVE BAM RESULTS | POSITIVE RESULTS WITH EXAMPLE METHOD |
|---|---|---|---|
| EGG PRODUCT | 19 | 3 | 9 |
| CHICKEN | 17 | 10 | 13 |
| PEPPER | 8 | 4 | 6 |
| SPICES | 8 | 6 | 7 |
| ONIONS | 6 | 5 | 6 |

The experimental method using the treatment composition of the example as a resuscitation medium again was superior to the conventional method when chicken meat was assayed for Salmonella. The control method determined 10 Salmonella contaminated samples while the experimental method found the presence of Salmonella in 13 samples. The experimental method also outperformed the control method in the testing of pepper, spices and onions. In addition to greater sensitivity than the control, the experimental method also provides a more rapid test for food pathogens, with results available within about 24 hours as opposed to two days with the BAM method.

The development of a resuscitation step utilizing the treatment composition of the present invention represents a new approach to improvements in food pathogen testing. Past approaches have focused upon improvements in the selective medium or in the application of ELISA and related technologies to reduce the amount of time required for testing. The resuscitation step instead provides a "front end" approach to reduce the time required for testing.

The present invention therefore provides versatile treatment compositions and methods effective in promoting the repair of injured, damaged or stressed cells. As can be readily appreciated, numerous variations and combinations of the features set forth above can be utilized without departing from the present invention as set forth in the claims. Such variations are not to be regarded as a departure from the spirit and scope of the invention, and all such modifications are intended to be included within the scope of the following claims.

We claim:

1. An anaerobic repair medium for the resuscitation of injured, damaged or stressed food pathogens, which medium comprises:
   a non-selective complete nutrient medium in an amount effective to supply all nutrients required by said food pathogens;
   a yeast derivative in an amount effective to promote the repair of said food pathogens;
   one or more antioxidants in an amount effective to promote the repair of said food pathogens;
   an oxygen tension reducing agent in an amount effective to reduce the oxygen tension of said nutrient medium to anaerobic levels; and
   one or more fatty acids required for membrane repair of said food pathogens between about 10 and about 25 carbon atoms in length and having from 0 up to 4 double bonds.

2. The repair medium of claim 1, wherein said complete liquid nutrient medium is selected from the group consisting of tryptic soy broth, nutrient broth, eagle's medium and yeast mold broth.

3. The repair medium of claim 1, wherein said complete liquid nutrient medium is present in an amount between about 2.5 and about 20 weight percent.

4. The repair medium of claim 1, wherein said one or more antioxidants are selected from the group consisting of pyruvate, succinate, gluthathione, catalase, selenium, albumen, glucose, BHA, BHT, ascorbic acid, lactic acid, uric acid, superoxide dismutase, glutathione peroxidase acid and n-acetyl cysteine.

5. The repair medium of claim 1, wherein said one or more antioxidants are present in an amount between about 0.10 and about 1.00 weight percent.

6. The repair medium of claim 1, wherein said one or more antioxidants include one or more membrane bound antioxidants.

7. The cell treatment composition of claim 6, wherein said one or more antioxidants are selected from the group consisting of vitamin E and beta-carotine.

8. The repair medium of claim 1, wherein said one or more antioxidants agent is selected from the group consisting of thioglycollate, cysteine and mixtures thereof.

9. The repair medium of claim 1, wherein said one or more antioxidants agent is present in an amount between about 0.0025 and about 0.50 weight percent.

10. The repair medium of claim 1, wherein at least one of said one or more fatty acids is unsaturated.

11. The repair medium of claim 10, wherein said one or more fatty acids are between 12 and 20 carbon atoms in length and have from 0 up to 3 double bonds.

12. The repair medium of claim 11, wherein said one or more fatty acids are supplied by one or more animal or vegetable fats.

13. The repair medium of claim 12, wherein said one or more fatty acids is supplied by chicken fat.

14. The repair medium of claim 13, wherein said one or more fatty acids are present in an amount between about 0.025 and about 1.0 weight percent.

15. The repair medium of claim 1, wherein said yeast derivative is selected form the group consisting of yeast extract, live yeast cell derivative, autolyzed yeast and mixtures thereof.

16. The repair medium of claim 1, wherein said yeast derivative is present in an amount between about 0.10 and about 1.0 weight percent.

17. The repair medium of claim 1, further comprising one or more protein supplements.

18. The repair medium of claim 17, wherein said one or more protein supplements are selected from the group consisting of casammino acids, brain-heart infusion, proteous peptone and mixtures thereof.

19. The repair medium of claim 17, wherein said one or more protein supplements are present in an amount between about 0.10 and about 1.0 weight percent.

20. A composition comprising:

from about 2.5 to about 20% by weight of a non-selective complete nutrient medium;

from about 0.10 to about 5.0% by weight of a yeast derivative selected from the group consisting of yeast extract, live yeast cell derivative and autolyzed yeast;

from about 0.10 to about 5% by weight of one or more antioxidants;

from about 0.0025 to about 5% by weight of an oxygen tension reducing agent; and from about 0.025 and about 5% by weight of chicken fat.

21. The composition of claim 20, comprising:
3.00 percent by weight tryptic soy broth;
0.50 percent by weight yeast extract;
0.25 percent by weight sodium pyruvate;
0.01 percent by weight sodium thioglycollate; and 0.10 percent by weight chicken fat.

22. AN anaerobic repair medium for the resuscitation of injured, damaged or stressed Salmonella, *E. coli*, *Staphylococcus aureus* and *Listeria monocytogenes* food pathogens, which medium comprises:

a non-selective complete nutrient medium in an amount effective to supply all nutrients required by said food pathogens;

a yeast derivative in an amount effective to promote the repair of said food pathogens;

one or more antioxidants in an amount effective to promote the repair of said food pathogens;

an oxygen tension reducing agent in an amount effective to reduce the oxygen tension of said nutrient medium to anaerobic levels; and 'one or more fatty acids required for membrane repair of said food pathogens between about 10 and about 25 carbon atoms in length and having from 0 up to 4 double bonds.

* * * * *

UNITED STATES PATENT AND TRADEMARK OFFICE
CERTIFICATE OF CORRECTION

PATENT NO. : 5,296,370

DATED : March 22, 1994

INVENTOR(S) : Martin et al.

It is certified that error appears in the above-identified patent and that said Letters Patent is hereby corrected as shown below:

On title page, item [56] under heading "PUBLICATIONS",
  lines 9-10, "Rutger University" should read --Rutgers University--.

Column 5, line 67, ".0%" should read --1.0%--.

Column 6, line 7, "so broth" should read --soy broth--.

Column 10, claim 4, line 3, after "succinate," "gluthathione" should read --glutathione--.

Column 10, claim 8, lines 1-2, "one or more antioxidants agent" should read --oxygen tension reducing agent--.

Column 10, claim 9, lines 1-2, "one or more antioxidants agent" should read --oxygen tension reducing agent--.

Column 10, claim 15, line 2, "is selected form" should read --is selected from--.

UNITED STATES PATENT AND TRADEMARK OFFICE
CERTIFICATE OF CORRECTION

PATENT NO. : 5,296,370
DATED : March 22, 1994
INVENTOR(S) : Martin et al.

It is certified that error appears in the above-identified patent and that said Letters Patent is hereby corrected as shown below:

Column 12, claim 22, line 1, "AN" should read --An--.

Column 12, claim 22, line 14, "and 'one" should read --and one--.

Signed and Sealed this

Twenty-sixth Day of July, 1994

Attest:

BRUCE LEHMAN

Attesting Officer    Commissioner of Patents and Trademarks